United States Patent [19]

Winston

[11] Patent Number: 5,163,939
[45] Date of Patent: Nov. 17, 1992

[54] DISK FLOW AND METHODS THEREFOR

[76] Inventor: Frederick Winston, 12087 Sheraton La., Cincinnati, Ohio 45246

[21] Appl. No.: 855,513

[22] Filed: Mar. 20, 1992

Related U.S. Application Data

[62] Division of Ser. No. 721,997, Jun. 27, 1991, Pat. No. 5,133,719.

[51] Int. Cl.⁵ ................ A61B 17/56; A61B 17/00
[52] U.S. Cl. .................... 606/61; 606/79; 606/84
[58] Field of Search ............ 606/79, 60, 61, 205–207, 606/99, 86, 90, 84; 623/17

[56] References Cited

U.S. PATENT DOCUMENTS

| | | | |
|---|---|---|---|
| 2,583,896 | 1/1952 | Siebrandt | 606/86 |
| 2,677,369 | 5/1954 | Knowles | 606/61 |
| 3,486,505 | 12/1969 | Morrison | 606/61 |
| 4,312,337 | 1/1982 | Donohue | 606/205 |
| 4,349,921 | 9/1982 | Kuntz | 623/17 |
| 4,545,374 | 10/1985 | Jacobson | 606/61 |
| 4,944,744 | 7/1990 | Ray | 606/90 |
| 4,955,885 | 9/1990 | Meyers | 606/61 |
| 5,015,247 | 5/1991 | Michelson | 606/61 |
| 5,019,081 | 5/1991 | Watanabe | 606/90 |

*Primary Examiner*—Michael A. Brown
*Attorney, Agent, or Firm*—Wood, Herron & Evans

[57] ABSTRACT

A medical instrument for engaging a fragment of disk tissue located anterior to the spinal cord and between two vertebrae which comprises an elongated handle member having first and second ends, and a slender curved member extending from the second end of the handle, with the slender curved member terminating in a blunt tip, which blunt tip is employed for engaging the disk tissue fragment. Preferably, the slender curved member has a radius of curvature of about 0.24", a thickness dimension of about 0.1", and is oriented with respect to the handle member at an angle of about 82.5°. It is further preferable that the blunt tip have a concavedly cylindrical surface with a radius of curvature of about 0.75", a width dimension in a plane parallel to its radius of curvature of about 0.38", and extend from the slender curved member by about 0.62 inches.

11 Claims, 1 Drawing Sheet

DISK PLOW AND METHODS THEREFOR

This is a division of application Ser. No. 721,997, filed Jun. 27, 1991, now U.S. Pat. No. 5,133,719.

FIELD OF THE INVENTION

This invention relates to medical instruments, and more particularly to a medical instrument for use during a diskectomy.

BACKGROUND OF THE INVENTION

Back surgery, and particularly the diskectomy procedure wherein a herniated disk is removed, has heretofore been difficult and cumbersome to perform due to the geometry of the operative site. Specifically, the operative site comprises a spinal cord, a plurality of vertebrae surrounding the spinal cord along its length, and disk tissue located between the vertebrae and anterior to the spinal cord. In a diskectomy procedure, the herniated disk which has encroached upon the spinal cord is sought to be removed. The disk tissue located on either side of the spinal cord is first severed and removed, then the remaining disk tissue or fragment of disk tissue located anterior to the spinal cord is severed and removed.

The most difficult part of the diskectomy procedure occurs when removing those remaining fragments of disk tissue located between the two vertebrae and anterior to the spinal cord. It will be appreciated that a surgeon's vision or line of sight is impaired in this part of the procedure, since for diskectomies the patient lies prone, and this causes the spinal cord to block the view of that portion of disk tissue or fragment of disk tissue which is sought to be removed.

Further complicating the diskectomy procedure is the rather sinuous nature of disk tissue. This disk tissue can therefore become evasive when a surgeon attempts to grasp or otherwise fixate this disk tissue with, for example, a forceps.

SUMMARY OF THE INVENTION

It has therefore been one objective of the present invention to provide a medical instrument wherein a diskectomy is facilitated when the disk tissue which is sought to be removed is located anterior to a patient's spinal cord.

It has been another objective of the present invention to provide a method by which a diskectomy may be performed when the disk tissue fragment which is sought to be removed is located anterior to the spinal cord.

The present invention is a medical instrument for engaging a fragment of disk tissue located anterior to a spinal cord and between two vertebrae which comprises an elongated handle having first and second ends, and a slender curved member extending from the second end of the handle, with the slender curved member terminating in a blunt tip, which blunt tip is employed for engaging the disk tissue fragment.

The instrument can be used to remove the fragment of disk tissue located anterior to the spinal cord by inserting a blunt end of a first instrument between the two vertebrae on one side of the spinal cord, inserting one end of a second instrument between the two vertebrae on another side of the spinal cord, and engaging the disk tissue fragment with the blunt end of the first instrument to push the disk tissue fragment to the second instrument. The fragment can then be grasped by the second instrument. Preferably, the second instrument is a forceps, and the first instrument comprises an elongated handle member having first and second ends, and a slender curved member extending from the second end of the handle, with the slender curved member terminating in a blunt tip, which blunt tip is utilized for engaging the disk tissue fragment.

A medical instrument of the present invention facilitates a diskectomy, particularly the removal of the disk tissue which is located anterior to a patient's spinal cord.

These and other objects and advantages of the present invention will become readily apparent during the following detailed description taken in conjunction with the drawings herein, in which:

DESCRIPTION OF THE PREFERRED EMBODIMENTS

Figure 1:
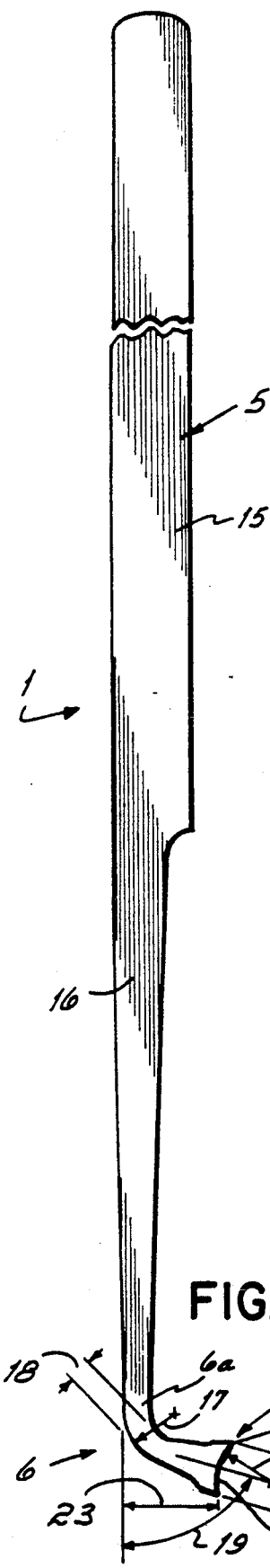
FIG. 1 is a side view of the medical instrument of the present invention.
Figure 2:
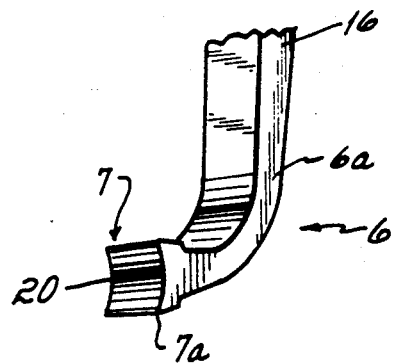
FIG. 2 is an enlarged perspective view of the blunt tip of the medical instrument of the present invention.

With reference to FIG. 1, there is illustrated the medical instrument of the present invention, or so-called disk plow 1. The disk plow 1 is preferably fabricated of a high grade stainless steel and comprises, generally, an elongated handle member 5, a slender curved member 6 extending from the lower end of the handle 5, and a blunt tip 7.

The handle 5 includes an upper grasping portion 15 and a lower tapered portion 16 which tapers from the grasping portion 15 gradually down to the slender curved member 6.

Slender curved member 6 has a radius of curvature 17 ranging from about 0.2 inches to about 0.3 inches, and preferably, is about 0.24". At approximately the midpoint 18 of this radius of curvature the slender member 6 has a thickness ranging from about 0.05 inches to about 0.2 inches, and preferably, is about 0.1". This slender curved member is oriented with respect to the handle member at an angle 19 ranging from about 70° to about 90°, and preferably, is about 82.5.

Blunt tip 7 has a disk tissue fragment engaging concavedly cylindrical surface 20. This concavedly cylindrical surface 20 has a radius of curvature 21 ranging from about 0.6 inches to about 0.9 inches, and preferably is about 0.75". This blunt tip 7 has a width dimension 22 in a plane parallel to its radius of curvature ranging between about 0.2 inches and about 0.5 inches, and preferably, is about 0.38". This is approximately the width between two adjacent vertebrae of an average patient. The forward edge 7a of the blunt tip 7 extends from the rear edge 6a of the curved member 6 by an amount ranging from about 0.5 inches to about 0.7 inches, and preferably is about 0.62 inches, as illustrated at 23.

Figure 3:
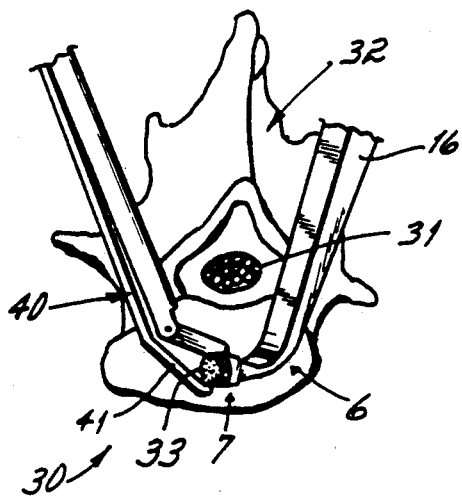
FIG. 3 is an illustration of the use of the medical instrument of the present invention.

With reference to FIG. 3, during a diskectomy, the operative site 30 includes a spinal cord 31, a plurality of vertebrae each surrounding the spinal cord along its length (one of which is shown at 32) and vertebral disks located between the vertebrae. FIG. 3 shows only a fragment of disk tissue located anterior to the spinal cord and between two of the vertebrae illustrated at 33.

After exposing the operative site, the portion of the disk which can readily be seen and removed is severed and separated from around the spinal cord. Then the remaining disk tissue fragment 33 located anterior to the spinal cord 31 is removed. To do so, the blunt tip of the disk plow 1 is inserted between two of the vertebrae on one side of the spinal cord 31, and then a forceps 40 is inserted between the two vertebrae on the other side of the spinal cord 31. The concavedly cylindrical surface 20 of the blunt tip 7 of the disk plow 1 is advanced against the disk tissue fragment 33, thereby engaging that disk tissue fragment 33 with the tip 7. The disk plow 1 is then employed to bias the disk tissue fragment 33 with the blunt tip 7 towards the jaw element 41 of the forceps 40, which jaw element 41 is in the open position. The disk tissue fragment 33 is then grasped with the forceps 40 by virtue of the jaw element 41, and may then be removed from between the two vertebrae.

To insert the disk plow 1 between the two vertebrae, it may be necessary to curette these two vertebrae with, for example, a reverse curette. Those skilled in the art will readily recognize the need for this procedure during the diskectomy.

In this procedure the size of the blunt end 7 of the disk plow 1 is about equal to the distance between two vertebrae. Therefore, the disk fragment cannot slip above or below the instrument. Further, the width of the instrument in conjunction with its concave surface prevents the disk fragment from slipping away from the instrument as the instrument is pushed against the fragment. Also, the length of the curved portion 6 enables the fragment to be pushed behind the spinal cord 31 and to be grasped by the forceps 40.

The present invention facilitates the removal of disk tissue or fragments of disk tissue located between two vertebrae and anterior to the spinal cord. Furthermore, a method has been provided wherein such disk tissue may readily be removed.

While I have described only one embodiment of the present invention, those skilled in the art will readily recognize adaptations and modifications which can be made to the present invention which will result in an improved medical instrument for performing diskectomies, yet without departing from the spirit or scope of the present invention. Accordingly, I intend to be limited only by the broad scope of the appended claims.

What is claimed is:

1. In an operative site including a spinal cord, a plurality of vertebrae surrounding said spinal cord along a length thereof, and disk tissue located between said vertebrae, a method of grasping a fragment of disk tissue located anterior to said spinal cord between two of said vertebrae comprising the steps of:
   exposing said operative site,
   inserting a first end of a first instrument between said two vertebrae on one side of said spinal cord,
   inserting a first end of a second instrument between said two vertebrae on another side of said spinal cord,
   engaging said disk tissue fragment with said first end of said first instrument,
   biasing said disk tissue fragment with said first end of said first instrument towards said first end of said second instrument, and
   grasping said disk tissue fragment with said first end of said second instrument.

2. The method of claim 1 wherein a space between said two vertebrae is enlarged with a reverse curette by curetting said two vertebrae.

3. The method of claim 1 wherein said second instrument is a forceps.

4. The method of claim 1 wherein said first instrument comprises:
   an elongated handle member having first and second ends, and
   a slender curved member extending from said second end of said handle, said slender curved member terminating in a blunt tip for engaging said disk tissue fragment.

5. The method of claim 4 wherein said handle member tapers gradually to said slender curved member.

6. The method of claim 5 wherein said slender curved member has a radius of curvature of about 0.24 inches.

7. The method of claim 6 wherein said slender curved member has a thickness dimension of about 0.1 inches.

8. The method of claim 7 wherein said slender curved member is oriented at an angle of about 82.5 degrees with respect to said handle member.

9. The method of claim 8 wherein said blunt tip has a disk tissue fragment engaging concavedly cylindrical surface, said surface having a radius of curvature of about 0.75 inches.

10. The method of claim 9 wherein said blunt tip has a width dimension in a plane parallel to said radius of curvature of said cylindrical surface of about 0.38 inches.

11. The method of claim 10 wherein a forward edge of said blunt tip extends from said slender curved member by about 0.62 inches.

* * * * *